(12) United States Patent
Carroll et al.

(10) Patent No.: US 10,793,423 B2
(45) Date of Patent: *Oct. 6, 2020

(54) MICROELECTROMECHANICAL ACCELEROMETER BASED SENSOR SYSTEM

(71) Applicant: Hartford Fire Insurance Company, Hartford, CT (US)

(72) Inventors: William Joseph Carroll, Vernon, CT (US); Bradley Dean Molinsky, Bloomfield, CT (US); Michael J. Dunst, Unionville, CT (US); Thomas Andrew Tipton, Milton, GA (US); Joseph S. Battaglini, Newington, CT (US)

(73) Assignee: Hartford Fire Insurance Company, Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/437,334

(22) Filed: Jun. 11, 2019

(65) Prior Publication Data
US 2019/0292044 A1    Sep. 26, 2019

Related U.S. Application Data

(63) Continuation of application No. 15/943,958, filed on Apr. 3, 2018, now Pat. No. 10,358,342, which is a
(Continued)

(51) Int. Cl.
*G08C 19/22* (2006.01)
*B81B 7/00* (2006.01)
*A61B 5/11* (2006.01)
*A61B 5/00* (2006.01)
*G16H 10/60* (2018.01)

(52) U.S. Cl.
CPC .......... *B81B 7/0087* (2013.01); *A61B 5/0022* (2013.01); *A61B 5/0024* (2013.01); *A61B 5/1118* (2013.01); *A61B 5/1123* (2013.01); *A61B 5/681* (2013.01); *A61B 5/7246* (2013.01); *A61B 5/7264* (2013.01); *G16H 10/60* (2018.01); *A61B 5/7282* (2013.01);
(Continued)

(58) Field of Classification Search
CPC ...... B81B 7/0087; B81B 7/007; G16H 10/60; A61B 5/0022; A61B 5/0024; A61B 5/1118; A61B 5/1123; A61B 5/681; A61B 5/7246; A61B 5/7264; A61B 5/7282; A61B 2560/0475; A61B 2562/0219; A61B 2562/028
USPC ..................................................... 340/870.07
See application file for complete search history.

(56) References Cited

U.S. PATENT DOCUMENTS

8,954,290 B2 *  2/2015  Yuen .................... A61B 5/6838
                                                    702/160
9,084,538 B2 *  7/2015  Yuen .................... G06F 19/3418
(Continued)

*Primary Examiner* — Kerri L McNally
*Assistant Examiner* — Thang D Tran
(74) *Attorney, Agent, or Firm* — Buckley, Maschoff & Talwalkar LLC (57) ABSTRACT

This invention relates to apparatus and systems for providing home and building security and condition monitoring. More particularly, the invention relates to a plurality of devices, including intelligent, multi-sensing, network-connected devices, that communicate dynamically with each other and a remote server.

22 Claims, 8 Drawing Sheets

Related U.S. Application Data continuation of application No. 15/590,278, filed on May 9, 2017, now Pat. No. 9,969,612, which is a continuation of application No. 14/970,744, filed on Dec. 16, 2015, now Pat. No. 9,655,547.

(52) U.S. Cl.
CPC .. *A61B 2560/0475* (2013.01); *A61B 2562/028* (2013.01); *A61B 2562/0219* (2013.01); *B81B 7/007* (2013.01)

(56) References Cited

U.S. PATENT DOCUMENTS

| | | | |
|---|---|---|---|
| 2008/0001735 A1* | 1/2008 | Tran | G06F 19/00 340/539.22 |
| 2009/0132197 A1* | 5/2009 | Rubin | G06F 15/177 702/141 |
| 2010/0241464 A1* | 9/2010 | Amigo | A61B 5/1038 705/4 |
| 2011/0046519 A1* | 2/2011 | Raheman | G06F 19/00 600/595 |
| 2012/0094649 A1* | 4/2012 | Porrati | A63B 24/0062 455/422.1 |
| 2012/0116548 A1* | 5/2012 | Goree | A61B 5/7239 700/90 |
| 2013/0106603 A1* | 5/2013 | Weast | H05K 5/0278 340/539.11 |
| 2013/0226486 A1* | 8/2013 | Henderson | H02J 7/0069 702/63 |
| 2014/0249379 A1* | 9/2014 | Proud | H02J 7/025 600/301 |
| 2015/0133748 A1* | 5/2015 | Edmonds | A61B 5/6806 600/301 |
| 2015/0156567 A1* | 6/2015 | Oliver | G08B 13/1427 340/870.07 |
| 2015/0279372 A1* | 10/2015 | Papierman | G09B 7/00 704/273 |
| 2016/0084869 A1* | 3/2016 | Yuen | A61B 5/681 73/510 |
| 2016/0228640 A1* | 8/2016 | Pindado | G06F 16/24 |
| 2017/0277138 A1* | 9/2017 | Kaji | A61B 5/1112 |

* cited by examiner

| Activity Level | Benefit Categorization | Activity Examples | Reference Levels |
|---|---|---|---|
| Level 0 | - Long Term | - No activity<br>- Sleeping, resting, sitting | - 0-1 kcals used per minute) |
| Level 1 | - Medium Term | - Light Activity<br>- Bowling, snowmobiling, painting, car washing, fishing, window cleaning, golf slow treading in pool | - 1-4 kcals used per minute) |
| Level 2 | - Short Term | - Moderate Activity<br>- Dancing: racquetball, tennis, volleyball, skiing easy, handball, yoga, recreational ice skating, recreational swimming | - 4-8 kcals used per minute) |
| Level 3 | - Normal | - Vigorous Activity<br>- Basketball, soccer, cross country skiing, martial arts, boxing, sparring, chopping wood, competitive swimming | - 8 + kcals used per minute |

MICROELECTROMECHANICAL ACCELEROMETER BASED SENSOR SYSTEM

CROSS-REFERENCE TO RELATED APPLICATIONS

The present application is a continuation of U.S. patent application Ser. No. 15/943,958 entitled "MICROELECTROMECHANICAL ACCELEROMETER BASED SENSOR SYSTEM" filed on Apr. 3, 2018 which was a continuation of U.S. patent application Ser. No. 15/590,278 entitled "MICROELECTROMECHANICAL ACCELEROMETER BASED SENSOR SYSTEM" filed on May 9, 2017 (issued as U.S. Pat. No. 9,969,612) which was a continuation of U.S. patent application Ser. No. 14/970,744 entitled "MICROELECTROMECHANICAL ACCELEROMETER BASED SENSOR SYSTEM" filed on Dec. 16, 2015 (issued as U.S. Pat. No. 9,655,547). The entire contents of those applications are incorporated herein by reference.

BACKGROUND

The use of portable electronic devices has grown exponentially recently, and in particular, the use of monitoring devices in sporting, health and work areas to measure activity levels, as well measuring environmental or user parameters such as temperature, heart rate, altitude, etc. has increased substantially. Sometimes, data related to user activities may be acquired from multiple devices, such as a smart phone, a GPS (Global Positioning System) device, a pedometer, a heart rate monitor, etc.

Microelectromechanical systems (MEMS) technology such as accelerometers for measuring acceleration and gyroscopes for measuring angular velocity have been implemented within several related devices and applications. For example, individual accelerometer and gyroscope based sensors are currently being used in mobile phones, gaming consoles, digital cameras, etc.

MEMS devices generally are capable of producing one or more analog output signals that correspond to a given measurement and, therefore, an analog-to-digital converter (ADC) is usually required to convert the analog output signals into corresponding digital signals for digital signal processing. Applications that include a MEMS device and an ADC, typically implement multi-chip board level technology to couple the MEMS device to the ADC, and/or implement the MEMS device and the ADC on separate chips, printed circuit boards (PCBs), or modules.

These devices enable the capture and collection of data that may be used in a variety of applications. It would be desirable to utilize these devices and information in more efficient and impactful applications.

SUMMARY

The present invention in some embodiments relates to a micro-electro-mechanical-system (MEMS) based sensor system for detecting and analyzing activity levels comprising a wireless router having a transceiver operable to communicate with at least one server programmed to operate as a world wide web server and having a network data adapter to communicate with one or more third party networks; and a wearable microelectromechanical sensor configured to connect to a mobile electronic device, the microelectromechanical sensor including a wireless communication transceiver provided internal to the microelectromechanical sensor wherein the microelectromechanical sensor wirelessly communicates with the mobile electronic device; the mobile electronic device configured to wirelessly receive and display user activity data collected by the microelectromechanical sensor, the mobile electronic device having a transceiver for transmitting the received user activity data to a remote server system device via a communications network, the remote server system configured to analyze the user activity data to determine an associated activity classification associated with the user activity data, each activity classification corresponding to a predetermined condition and an associated condition benefit, the mobile electronic device enabled to transmit instructions to microelectromechanical sensor in order to vary a sampling condition of the microelectromechanical sensor in response to the determined activity classification.

In other embodiments, the present invention relates to a microelectromechanical sensor based system for measuring activity levels comprising at least one wearable microelectromechanical sensor configured within a mobile electronic device, the microelectromechanical sensor including a wireless communication transceiver provided internal to the microelectromechanical sensor for transmitting the measured user activity data to a remote server system device via a communications network, the remote server system configured to analyze the user activity data to determine an associated activity classification associated with the user activity data, each activity classification corresponding to a predetermined condition and an associated condition benefit, wherein the determined activity classification determines a content of one or more electronic communications transmitted by the remote server system to a user device.

In further embodiments, the present invention related to a microelectromechanical sensor based system comprising an accelerometer based sensor configured to connect to a mobile electronic device, the accelerometer based sensor including a wireless communication transceiver provided internal to the accelerometer sensor wherein the accelerometer based sensor wirelessly communicates with the mobile electronic device; the mobile electronic device configured to wirelessly receive user activity data collected by the accelerometer based sensor, the mobile electronic device having a transceiver for transmitting the received user activity data to a remote server system device via a communications network, the received user activity data triggering a pricing parameter adjustment associated with the user, the remote server system configured to analyze the user activity data to determine an associated activity classification associated with the user activity data, the mobile electronic device enabled to transmit instructions to the accelerometer based sensor in order to validate the determined activity classification.

BRIEF DESCRIPTION OF THE DRAWINGS

A more detailed understanding may be had from the following description, given by way of example in conjunction with the accompanying drawings wherein.

DETAILED DESCRIPTION

Disclosed herein are apparatuses and computing systems to provide a Microelectromechanical Systems (MEMS) device and interface for business and the like, wherein the device and interface is provided for user identification and activity verification that communicates in accordance with various protocol standards. The device and interface can accept data from one or more activity detections sensors and can also use various combinations of sensors, thereby providing a high level of accuracy and integrity. The device and interface is preferably housed internally or externally as part of a portable device, such as a mobile telephone. The device and interface of the present invention provides mutual communication between the user and a third party server for processing and evaluation in accordance with various protocol standards. There is thus provided in accordance with a preferred embodiment of the present invention a device and interface including an input interface operative to receive activity data signals, an output component operative to convert the data signals into converted signals suitable for transmission to a wireless router, in accordance with any protocol standard selected from a plurality of standards that define how a wireless signal is transmitted from the device to a service provider network, the wireless router including transmitter in communication with the output component operative to transmit to a third party server.

Figure 1:
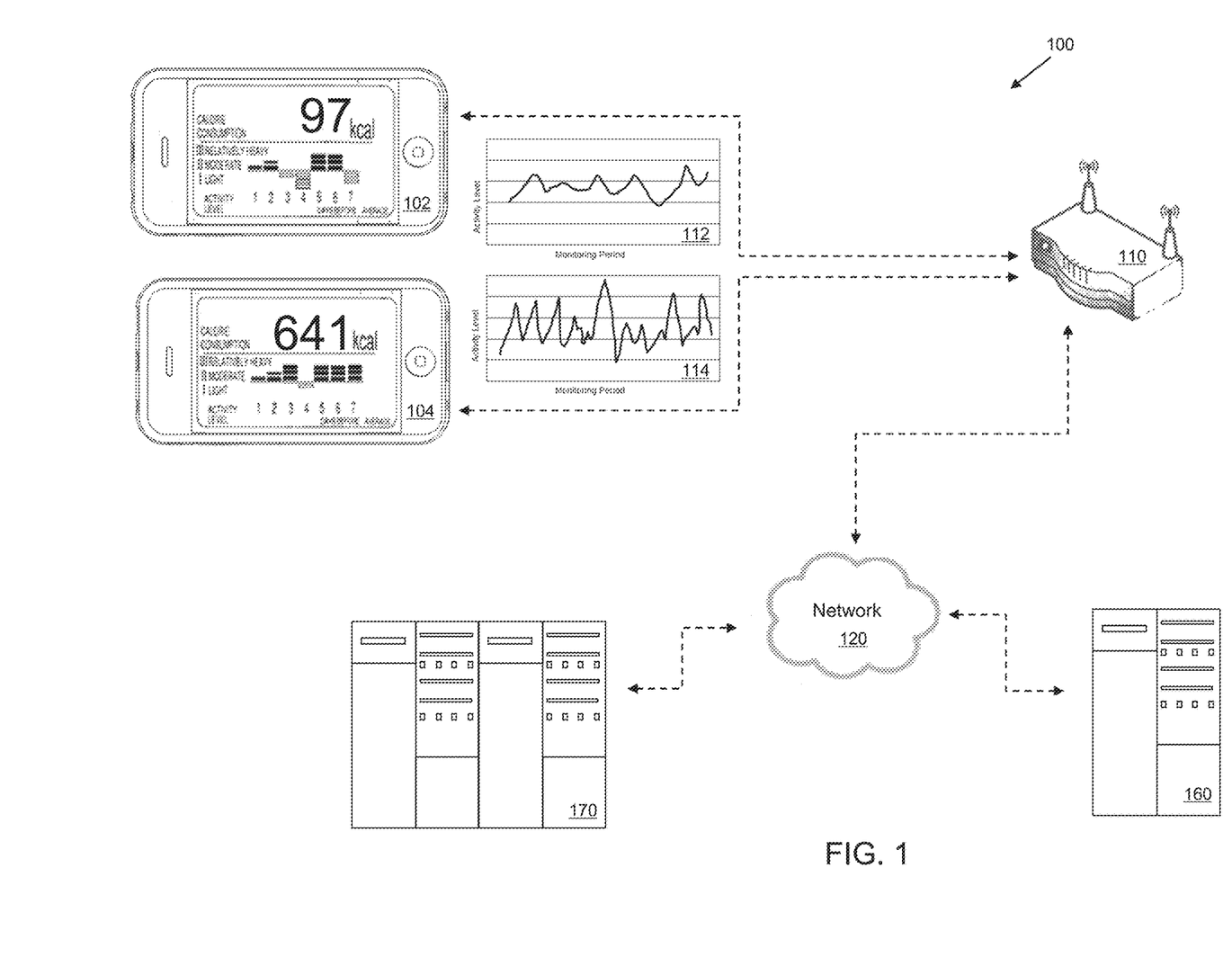
FIG. 1 shows an exemplary system architecture of the present invention.

Referring to FIG. 1, a dynamic sensor system 100 for mobile devices 102 and 104 configured according to exemplary embodiments, and having activity monitoring and wireless positioning capability, will be described. Dynamic sensor system 100 may include one or more different types of activity monitoring components and systems such as MEMS based accelerometer and acceleration sensing systems, wireless communication systems and/or wireless positioning systems. Dynamic sensor system 100 may be configured to in accordance with embodiments of the present invention to collect, detect and/or measure one or more of the following types of activity information: pulse, heart rate, pulse rate, breathing rate, blood flow, metabolism, electrolyte type and/or concentration, physical activity, caloric intake, caloric metabolism, blood pH level, physical and/or psychological stress levels and/or stress level indicators, position and/or balance, body strain, neurological functioning, brain activity, brain waves, blood pressure, temperature, eye muscle movement, blood volume, inhaled and/or exhaled breath volume, physical exertion, exhaled breath physical and/or chemical composition, psychological mood, sleep patterns, hunger and/or thirst, hormone type and/or concentration, cholesterol, lipids, blood panel, bone density, organ and/or body weight, reflex response, sexual arousal, mental and/or physical alertness, sleepiness, voice characteristics, voice tone, voice pitch, voice volume, vital signs, head tilt, allergic reactions, inflammation response, auto- immune response, mutagenic response, DNA, proteins, protein level, digestive system functioning and/or other physiological information.

Wireless signals from satellites or GNSS sources may be used for trilateration of mobile devices 102 and 104. One or more terrestrial sources, such as cellular base stations, Wide Area Network Wireless Access Points (WAN-WAPs), wide area wireless network (WWAN), WiMAX (e.g., 802.16), etc. may be used for wireless voice and/or data communication, and as another source of activity and position information for mobile devices 102 and 104. One or more other wireless signal sources such as Local Area Network Wireless Access Points (LAN-WAPs), WLAN, Wi-Fi networks (802.11x), cells, Bluetooth Networks, etc. which may be used for wireless voice and/or data communication, as well as yet another source for activity and positioning data. Devices 102 and 104 may operate in outdoor and indoor environments, such as buildings, and capable of performing communications over smaller geographic regions than a WWAN, for example. Mobile device 102 and 104 may detect activity type information as well as derive position information from any one or more of sources can conform to other types of positioning.

A Wireless Local Area Network (WLAN) transceiver, router or base station 110 may be connected to one or more networks 120 for communicating with and/or detecting signals to/from mobile device 102 and 104. The wireless router 100 may include a wireless transceiver for accessing a wireless packet data channels and/or a network interface for coupling to an Internet Protocol (IP) based network. The network interface preferably includes a conventional short range wireless transceiver, such as a Bluetooth transceiver, a Home RF transceiver, a wireless IP 801.11 transceiver, and/or ETSI HyperLANx transceiver for coupling to network 120, such as a WLAN. The network interface can include a wired transceiver, such as a Fast Ethernet transceiver, or a modem, for interconnecting with a wired Local Area Network (LAN).

Network 120 may also be connected to the one or more antennas for receiving satellite or radio frequency signals. Wireless base station 110 may provide connectivity via network 120 to one or more third party servers 160 and 170.

Referring still to FIG. 1, mobile devices 102 and 104 may have one or more incorporated motion/activity sensors which may be coupled to processor to provide movement, position, activity and/or orientation information. Mobile devices 102 and 104 may capture and output movement, position, activity and/or orientation data such as activity data 112 and 114 associated with devices 102 and 104. By way of example, a motion/activity sensor may utilize motion sensors such as an accelerometer such as a MEMS device, a gyroscope, a geomagnetic sensor such as a compass, an altimeter such as a barometric pressure altimeter, and/or any other type of movement detection sensor. In exemplary embodiments, motion sensor may utilize one or more components or features derived from motion sensors, such as, a pedometer to detect a number of walking/step counts, and/or a motion detector to classify/detect motion modes such as sedentary, running, jumping, walking, etc. Moreover, motion sensor may include a plurality of different types of devices and combine their outputs in order to provide motion information. For example, the motion sensor may use a combination of a multi-axis accelerometer and orientation sensors to provide the ability to compute positions in two dimensional and/or three dimensional coordinate systems. In the present invention, activity data 112 and 114 may be captured and via device 102 and 104 and transmitted via router 110 through network 120 to servers 160 and 170 for validation, processing and analysis to determine if the activity levels detected are consistent with predictive or anticipated levels for the user.

Figure 2:
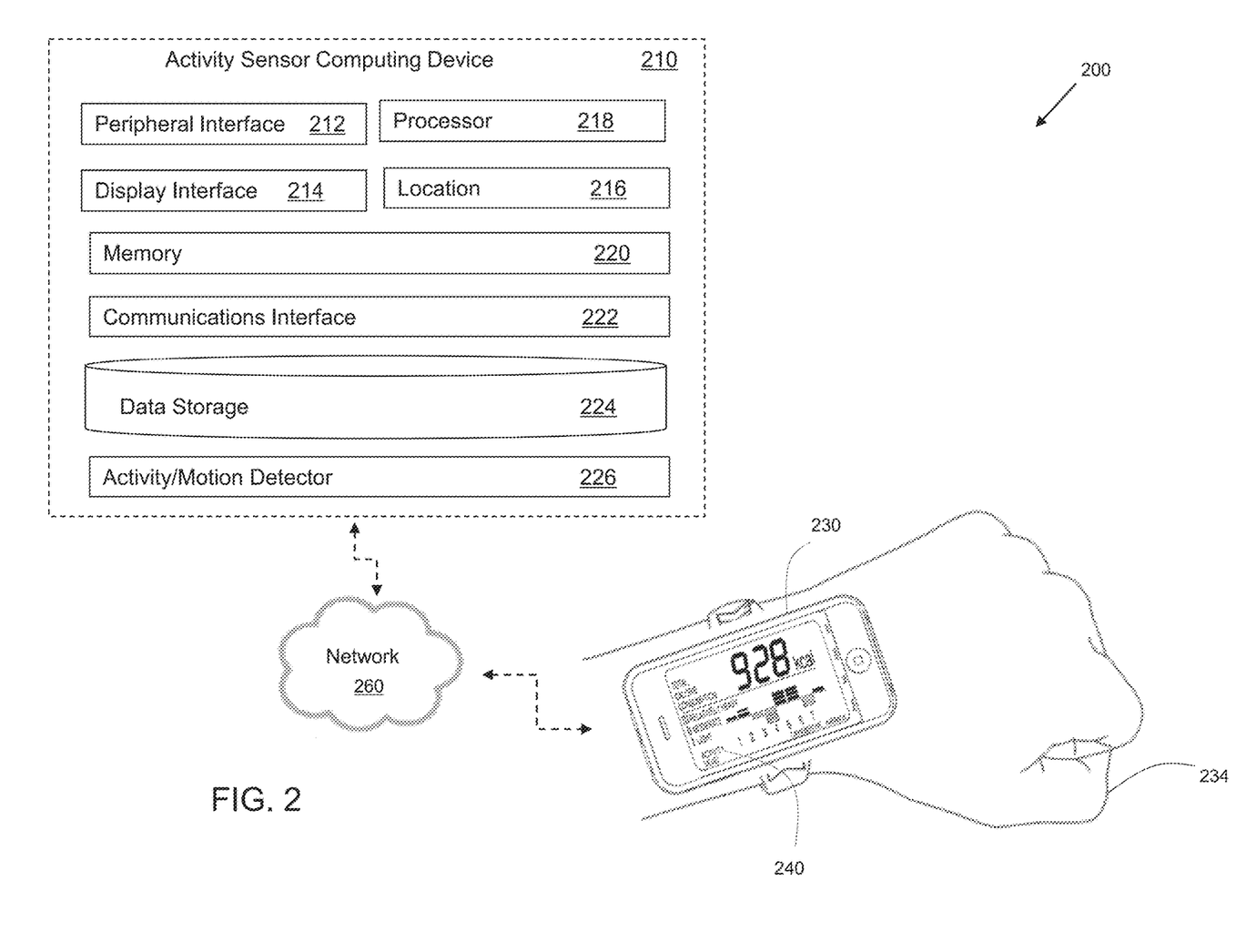
FIG. 2 shows an exemplary system that may be used for the management and analysis of sensor data.

FIG. 2 shows an example system architecture 200 that may be used for activity and motion sensor capture and analysis in accordance with the present invention. FIG. 2 shows an example activity sensor computing device 210 that may be used to implement features describe above for managing building and risk data in accordance with embodiments of the present invention. Computing device 210 may be integrated as part of or completely integrated with an individual computing mobile device 230 associated with a user 234 in some embodiments.

Referring still to FIG. 2, the computing device 210 may include a peripheral device interface 212, a display device interface 214, a navigation/location component 216, a processor 218, a memory device 220, a communication interface 222, a data storage 224 and an activity/motion detector component 226. In operation, computing device 210 is configured to receive and transmit a number of signals via communications interface 222 including, for example, data, image, sound and/or video data related to one or more user's activity levels.

Processor 218 may include one or more microprocessors, microcontrollers, and/or digital signal processors that provide processing functions, as well as other calculation and control functionality. Processor 218 may include any form of logic suitable for performing the processes and instructions provided herein. For example, the processor 218 may be operatively configurable based on instructions in the memory 220 to selectively initiate one or more routines that capture and analyze motion/activity data.

The peripheral device interface 212 may be an interface configured to communicate with one or more peripheral devices such as a variety of sensors, device, cameras and modules. The peripheral device interface 212 may operate using a technology such as Universal Serial Bus (USB), PS/2, Bluetooth, infrared, firewire, serial port, parallel port, and/or other appropriate technology. Additionally, the peripheral device interface 212 may, for example, receive input data from an input device such as a keyboard, a mouse, a trackball, a touch screen, a touch pad, a stylus pad, and/or other device. Alternatively or additionally, the peripheral device interface 212 may communicate output data to a printer that is attached to the computing device 210 via the peripheral device interface 212.

The display device interface 214 may be an interface configured to communicate data to display device 234. The display device 234 may be, for example, a monitor or television display, a plasma display, a liquid crystal display (LCD), and/or a display based on a technology such as front or rear projection, light emitting diodes (LEDs), organic light-emitting diodes (OLEDs), or Digital Light Processing (DLP). The display device interface 214 may operate using technology such as Video Graphics Array (VGA), Super VGA (S-VGA), Digital Visual Interface (DVI), High-Definition Multimedia Interface (HDMI), or other appropriate technology. The display device interface 214 may communicate display data from the processor 218 to the display device 214 for display by the display device 234. As shown in FIG. 2, the display device 214 may be external to the computing device 210, and coupled to the computing device 210 via the display device interface 214.

The memory device 220 of FIG. 1 may be or include a device such as a Dynamic Random Access Memory (D-RAM), Static RAM (S-RAM), or other RAM or a flash memory. The storage device 224 may be or include a hard disk, a magneto-optical medium, an optical medium such as a CD-ROM, a digital versatile disk (DVDs), or Blu-Ray disc (BD), or other type of device for electronic data storage.

The communication interface 222 may be, for example, a communications port, a wired transceiver, a wireless transceiver, and/or a network card. The communication interface 222 may be capable of communicating using technologies such as Ethernet, fiber optics, microwave, xDSL (Digital Subscriber Line), Wireless Local Area Network (WLAN) technology, wireless cellular technology, and/or any other appropriate technology. Communications interface may provide connectivity to and/or from mobile device 230.

Mobile device 230 may include user display interface 240 which provides suitable interface systems, such as microphone/speaker, keypad, and display that allows user interaction with computing device 210. As used herein, mobile device 230 may be any portable or movable wireless device or machine that is configurable to acquire wireless signals transmitted from, and transmit wireless signals to, one or more wireless communication devices or networks. As used herein, the term "wireless device" may refer to any type of wireless communication device which may transfer information over a network and also have activity, position determination and/or navigation functionality. The wireless device may be any cellular mobile terminal, personal communication system (PCS) device, personal navigation device, laptop, personal digital assistant, or any other suitable mobile device capable of receiving and processing network and/or GNSS signals such as via wireless network 260.

Wireless network 260 may be implemented using any wireless data transmission including but not limited to TDMA, GSM, CDPD, GPRS, EDGE, and UMTS. In a preferred embodiment, a data communications link layer is implemented using one of these technologies, a data communications network layer is implemented with the Internet Protocol ("IP"), and a data communications transmission layer is implemented using the Transmission Control Protocol ("TCP"). In such systems, information between the devices and control device 230 are transmitted using an application-level protocol such as, for example, the Hyper-Text Transmission Protocol ("HTTP"), the Wireless Application Protocol ("WAP"), the Handheld Device Transmission Protocol ("HDTP"), or any other data communications protocol as will occur to those of skill in the art.

As used herein, "TDMA" stands for Time Division Multiple Access, a technology for delivering digital wireless service using time-division multiplexing. "GSM" stands for Global System for Mobile Communications, a digital cellular standard in Europe and Asia. "CDPD" stands for Cellular Digital Packet Data, a data transmission technology developed for use on cellular phone frequencies. "GPRS" stands for General Packet Radio Service, a standard for wireless data communications that supports a wide range of speeds, is an efficient use of limited bandwidth and is particularly suited for sending and receiving small bursts of data, such as e-mail and Web browsing, as well as large volumes of data. "EDGE" stands for Enhanced Data Rates for GSM Evolution, a standard for wireless data communications supporting high data transfer rates. "UMTS" stands for Universal Mobile Telecommunication System, a standard for wireless data communications supporting high data transfer rates and also referred to as W-CDMA for Wideband Code Division Multiple Access.

Alternatively or additionally, an instance of the computing device 210 may be configured to perform any feature or any combination of features described herein. In such an instance, the memory device 220 and/or the storage device 224 may store instructions which, when executed by the processor 218, cause the processor 218 to perform any feature or any combination of features described herein. In such an instance, the processor 218 may perform the feature or combination of features in conjunction with peripheral device interface 212, display interface 214, memory 220, communication interface 222, and/or data storage device 224.

Although FIG. 2 shows that the computing device 210 includes a single processor 218, single memory device 220, single communication interface 222, single peripheral device interface 212, single display device interface 214, and single storage device 224, the computing device may include multiples of each or any combination of these components and may be configured to perform analogous functionality to that described above.

In the present invention, display interface 214 may be operable to provide a display such as display 240 that are capable of displaying indicia representative of measured and calculated activity and physiological parameters such as one or more of a activity level, calories burned, pulse rate, etc. User display 240 may also be capable of storing or displaying expected historical or activity trending data related to one or more of the measured data or parameters or combinations of the measured data and parameters. For example, if a user's measured activity level deviates from an expected level, then the user may receive a warning or other type of message on device 230.

Each or any combination of the components/modules shown in FIG. 2 may be implemented as one or more software modules or objects, one or more specific-purpose processor elements, or as combinations thereof. Suitable software modules include, by way of example, an executable program, a function, a method call, a procedure, a routine or sub-routine, one or more processor-executable instructions, an object, or a data structure. In addition or as an alternative to the features of these modules described above with reference to FIG. 2, these modules may perform functionality described later herein.

Figure 3:
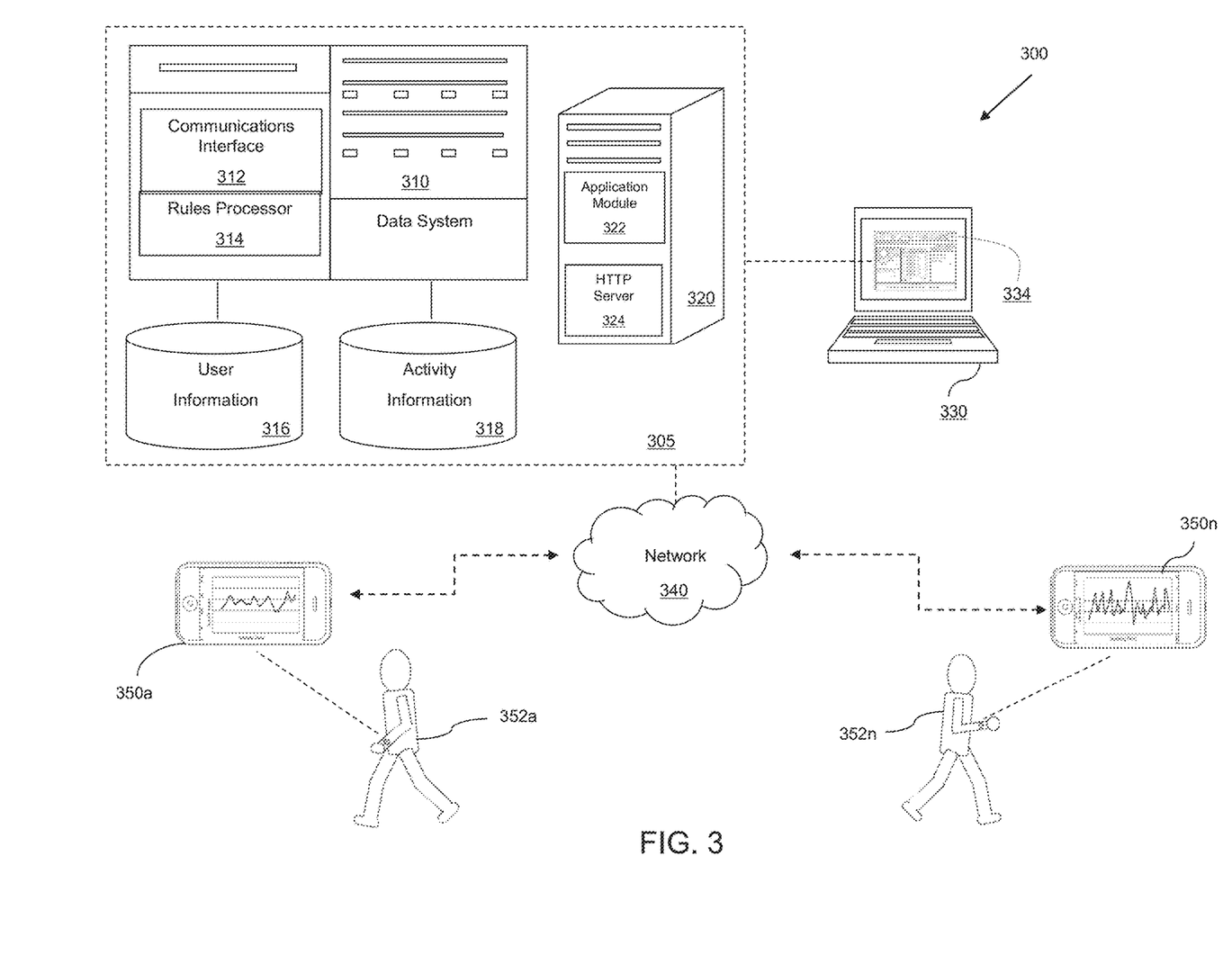
FIG. 3 shows another exemplary system of the present invention.

FIG. 3 shows an overall exemplary system architecture 300 that may be used for activity detection and analysis using sensor based data. The example architecture 300 includes a computer system 305 including a data system 310, a web system 320 and a business terminal 330, a network 340, and a plurality of mobile sensor computing devices 350*a*-*n* associated with a plurality of users 352*a*-*n*. Although, only two sensor computing devices are shown, three or more sensor computing devices may be utilized in the present invention. Sensor device may include electro-mechanical type or MEMS type activity sensors that use one or more accelerometers and microprocessors properly programmed to detect user activity. These activity sensors generally have 1-, 2- or 3-axis accelerometers to measure accelerations and generate electronic signals corresponding to physical movement of the users. The software in the microprocessor then processes the electronic acceleration signals to determine activity levels. Data system 310 may include a communications interface 312, a rules processor 314, a user database 316 and an activity information database 318.

In one embodiment, business rules processor 314 may include one or more rules and/or predictive models. The rules processor 314 may use the one or more rules and/or predictive models to evaluate activity data as well as customer data to determine, for example, if an exception condition occurs such as a potential fraudulent condition related to the activity level of one or more of the users 352*a*-*n*. Generally, a predictive model takes into account a plurality of parameters, and in embodiments may take into account any number of parameters, such as up to 10 parameters, up to 100 parameters or several hundred or more parameters. The predictive model may include one or more of neural networks, Bayesian networks (such as Hidden Markov models), expert systems, decision trees, collections of decision trees, support vector machines, or other systems known in the art for addressing problems with large numbers of variables. Preferably, the predictive model is trained on prior data and outcomes. The specific data and outcomes analyzed vary depending on the desired functionality of the particular predictive model. The particular data parameters selected for analysis in the training process are determined by using regression analysis and/or other statistical techniques known in the art for identifying relevant variables in multivariable systems.

In other embodiments, one or more decision trees, equations or tables may be included with and executed by rules processor 314. Decision trees may include decisions relating to identified terms and phrases and equivalent terms and phrases, in accordance with text based analysis principles.

In one embodiment, data system 310, terminal 330, and remote device 350*a*-*n* are in communication via a network 340. Data system 310 shown in FIG. 3 is an embodiment of a system that might be implemented solely within a single location or be an aggregation of one or more other subsystems including one or more partner, third party administrator and/or vendor subsystems to allow communications and data transfer between the company and representatives, investigators, adjusters, customers, and agents. Data transferred through network 340 to system 310 may pass through one or more firewalls or other security type controls implemented within web system 320 and/or in standalone devices. The firewall allows access to network 340 only through predetermined conditions/ports. In another embodiment, the firewall restricts the Internet IP addresses that may access web system 320.

Referring to FIG. 3 still, rules processor 314 may include one or more business rules and one or more predictive models, decision trees, equations and/or tables, in conjunction with one or more software modules or objects and one or more specific-purpose processor elements, to perform the processing required by embodiments of the present invention such as for evaluating sensor data.

The user information database 316 may store information, data and documents that relate to customers such as group benefits information as well as location information. In the present invention, location information may also be used in conjunction with detected activity information to determine if the user is within permissible activity levels. For example, if the user is at a location that requires activity levels that are not within predicted or expected activity levels for the user then the location may be indicative of an exception condition. Activity information database 318 may store information, data and documents from user devices 350*a*-*n* and remote devices 350*a*-*n*. User information database 316 and activity information database 318 may be spread across one or more computer-readable storage media, and may be or include one or more relational databases, hierarchical databases, object-oriented databases, one or more flat files, one or more spreadsheets, and/or one or more structured files. User information database 316 and activity information database 318 may be managed by one or more database management systems (not depicted), which may be based on a technology such as Microsoft SQL Server, MySQL, Oracle Relational Database Management System (RDBMS), PostgreSQL, a NoSQL database technology, and/or any other appropriate technology. Communication between the data system 310 and the other elements in the example architecture 300 of FIG. 3 may be performed via the communications interface module 312.

Referring still to FIG. 3, web system 320 may provide a web interface that may be accessed directly by a user such as an insured, a claims representative, an adjuster and other third party entity employing user devices 332a-n to communicate and interact with a company representative employing terminal 330. In certain embodiments, terminal 330 can include, but are not limited to cellular telephones, other wireless communication devices, personal digital assistants, pagers, laptop computers, tablet computers, smartphones, other mobile display devices, or combinations thereof. In embodiments of the present invention, terminal 330 may communicate with the web site system 320 that may be operated by or under the control of an entity or other third party entity such as an outsourced type entity or third party administrator type entity.

The web site system 320 may include a web application module 322 and a HyperText Transfer Protocol (HTTP) server module 324. The web application module 322 may generate the web pages that make up the web site and that are communicated by the HTTP server module 324. Web application module 322 may be implemented in and/or based on a technology such as Active Server Pages (ASP), PHP: Hypertext Preprocessor (PHP), Python/Zope, Ruby, any server-side scripting language, and/or any other appropriate technology.

The HTTP server module 324 may implement the HTTP protocol, and may communicate HyperText Markup Language (HTML) pages and related data from the web site to/from client devices terminal 334, user device 350c, using HTTP. The HTTP server module 324 may be, for example, a Sun-ONE Web Server, an Apache HTTP server, a Microsoft Internet Information Services (IIS) server, and/or may be based on any other appropriate HTTP server technology. The web site system 320 may also include one or more additional components or modules (not depicted), such as one or more switches, load balancers, firewall devices, routers, and devices that handle power backup and data redundancy.

Referring still to FIG. 3, terminal 330 may include a web browser module 334, which may communicate data related to the web site to/from the HTTP server module 324 and the web application module 322 in the web site system 320. The web browser module 334 may include and/or communicate with one or more sub-modules that perform functionality such as rendering HTML (including but not limited to HTML5), rendering raster and/or vector graphics, executing JavaScript, and/or rendering multimedia content. Alternatively or additionally, the web browser module 334 may implement Rich Internet Application (MA) and/or multimedia technologies such as Adobe Flash, Microsoft Silverlight, and/or other technologies. The web browser module 334 may implement MA and/or multimedia technologies using one or web browser plug-in modules (such as, for example, an Adobe Flash or Microsoft Silverlight plugin), and/or using one or more sub-modules within the web browser module 334 itself.

The example architecture 300 of FIG. 3 may also include one or more wired and/or wireless networks via which communications between the elements and components shown in the example architecture 300 may take place. The networks may be private or public networks, cloud or shared networks and/or may include the Internet. In one embodiment, thousands and even millions of users 352a-n are simultaneously transmitting activity data via devices 350a-n via network 340 for processing via data system 310.

Figure 4:
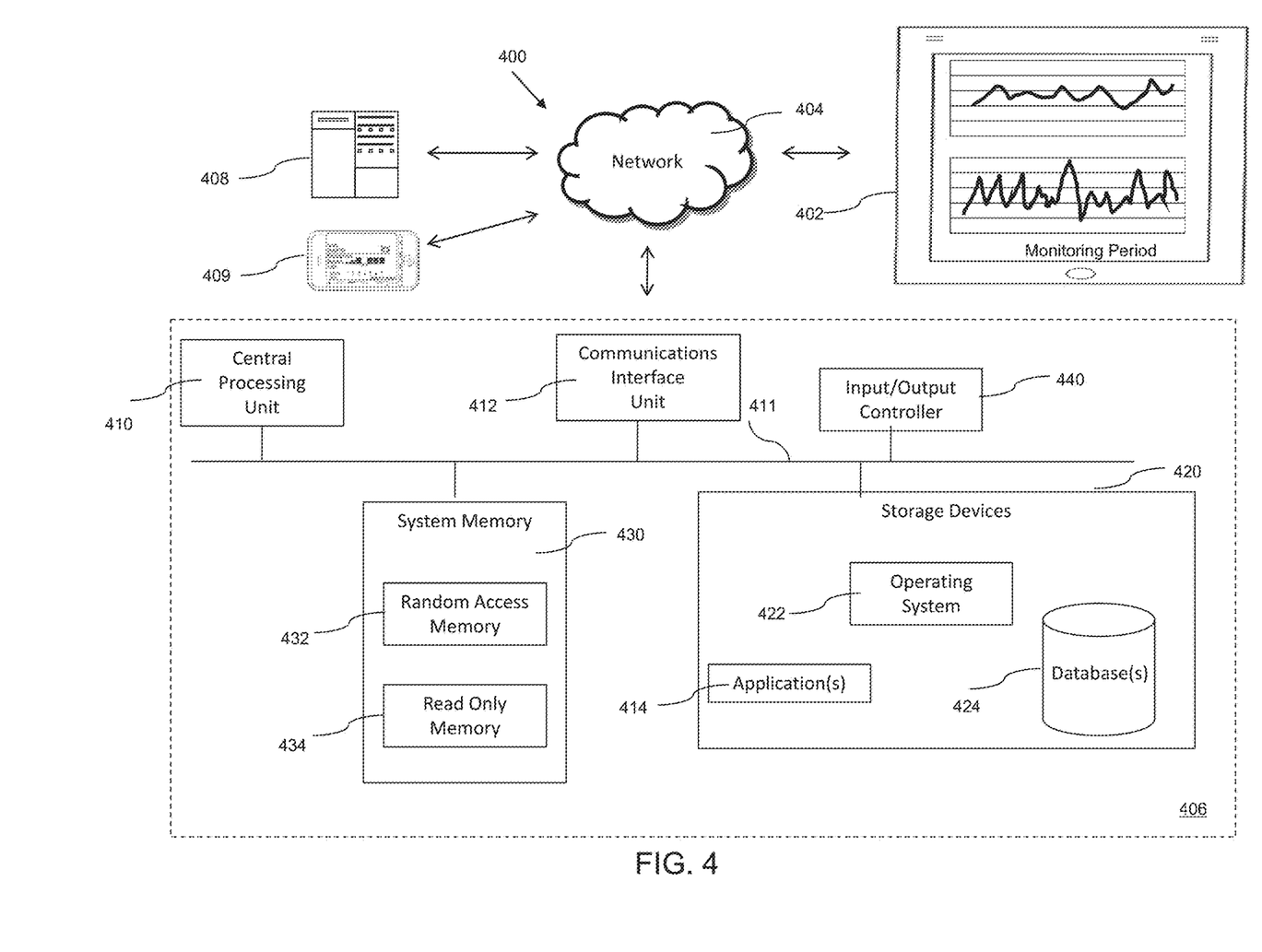
FIG. 4 shows another exemplary system embodiment of the present invention.

Referring to FIG. 4, an exemplary computer system 400 for use in an implementation of the invention will now be described. Computer system 400 may be configured to perform pricing, risk management, loss control services and claims evaluation and management for one or more companies and their associated agents, personnel, customers and staff using devices 402. System 400 may include device 402, which may be a company agent or vendor terminal or device, a network 404, a processing and data system 406 and one or more third party servers 408 and one or more activity sensors 409. In embodiments of the present invention, processing and data system 406 is responsible for the processing of user activity and motion data to adjust pricing parameters associated with a group benefits offering. Third party servers may be administered by third party web operators or social media server operators.

In processing and data system 406, a central processing unit or processor 410 executes instructions contained in programs such as a benefits management application program 414, stored in storage devices 420. Processor 410 may provide the central processing unit (CPU) functions of a computing device on one or more integrated circuits. As used herein, the term "processor" broadly refers to and is not limited to a single- or multi-core general purpose processor, a special purpose processor, a conventional processor, a Graphics Processing Unit (GPU), a digital signal processor (DSP), a plurality of microprocessors, one or more microprocessors in association with a DSP core, a controller, a microcontroller, one or more Application Specific Integrated Circuits (ASICs), one or more Field Programmable Gate Array (FPGA) circuits, any other type of integrated circuit (IC), a system-on-a-chip (SOC), and/or a state machine.

Storage devices 420 may include suitable media, such as optical or magnetic disks, fixed disks with magnetic storage (hard drives), tapes accessed by tape drives, and other storage media. Processor 410 communicates, such as through bus 411 and/or other data channels, with communications interface unit 412, storage devices 420, system memory 430, and input/output controller 440. System memory 430 may further include non-transitory computer-readable media such as a random access memory 432 and a read only memory 434. Random access memory 432 may store instructions in the form of computer code provided by application 414 to implement embodiments of the present invention. One or more computer programs may be stored in memory, or computer usable media, such as storage devices 420 and random access memory 432, in the form of computer readable program code adapted to be executed by at least one processor, such as a central processing unit 410. The one or more computer programs may include instructions for performing steps of methods of embodiments of the invention described herein. System 400 further includes an input/output controller 440 that may communicate with processor 410 to receive data from user inputs such as pointing devices, touch screens, and audio inputs, and may provide data to outputs, such as data to video drivers for formatting on displays, and data to audio devices.

Storage devices 420 are configured to exchange data with processor 410, and may store programs containing processor-executable instructions, and values of variables for use by such programs. Processor 410 is configured to access data from storage devices 420, which may include connecting to storage devices 420 and obtaining data or reading data from the storage devices, or placing data into the storage devices. Storage devices 420 may include local and network accessible mass storage devices. Storage devices 420 may include media for storing operating system 422 and mass storage devices such as storage 424 for storing data related to sensor data, including sensor activity information, GIS data and other location based data, policy data including location data, such as physical address data, and address data such as telephone number data and e-mail address data, predictive model data, and user related data.

Communications interface unit 412 may communicate via network 404 with other computer systems such as third party servers 408 as well as other internal and external servers, computer systems of remote sources of data, and with systems for implementing instructions output by processor 410. Processing and data system 406 may also be configured in a distributed architecture, wherein databases, data storage devices and processors are housed in separate units or locations. The servers perform primary processing functions and contain at a minimum, a RAM, a ROM, and a general controller or processor. In such an embodiment, each of these servers is attached to a communications hub or port that serves as a primary communication link with other servers, client or user computers and other related devices. The communications hub or port may have minimal processing capability itself, serving primarily as a communications router. A variety of communications protocols may be part of the system, including but not limited to: Ethernet, SAP, SASTM, ATP, Bluetooth, GSM and TCP/IP. Network 404 may be or include wired or wireless local area networks and wide area networks, and over communications between networks, including over the Internet.

One or more public cloud, private cloud, hybrid cloud and cloud-like networks may also be implemented, for example, to handle and conduct processing of one or more transactions or processing of embodiments of the present invention. Cloud based computing may be used herein to handle any one or more of the application, storage and connectivity requirements of embodiments of the present invention. For example one or more private clouds may be implemented to store, process and otherwise handle sensor data and discount data of embodiments of the present invention. Furthermore, any suitable data and communication protocols may be employed to accomplish the teachings of embodiments of the present invention.

Figure 5:
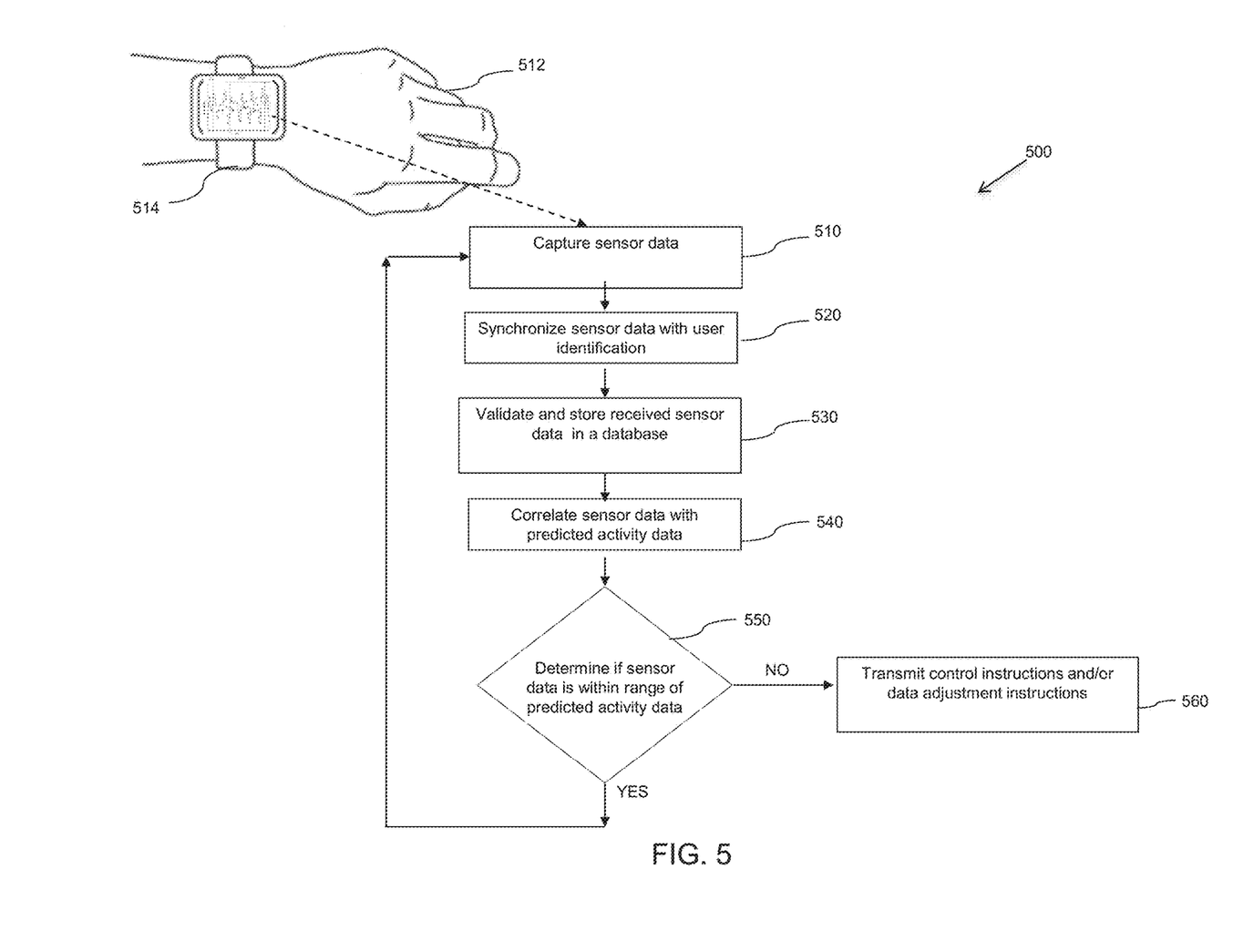
FIG. 5 shows a process flow diagram of an exemplary computer implemented method in accordance with the present invention.

FIG. 5 illustrates an exemplary computerized method 500 of the present invention. In one embodiment, the method 500 includes the step capturing sensor data, step 510. Sensor data may be captured from one or more users 512 that are utilizing one or more MEMS sensor devices 514. The method further continues with synchronizing sensor data with user identifications, step 520. The method continues with validating and storing sensor data in a database, step 530. The method continues with correlating sensor data with predicted activity data, step 540. The system determines if the sensor data is within range of predicted activity data, step 550. For example, if a user's very vigorous activity is correlated with predicted sedentary activity then an exception condition may be determined. Accordingly, the system transmits instructions to the sensor device, step 560. For example, if the data includes an indication of a deviation, violation or a breach of a threshold, information may be sent to the sensor to capture additional information or data. Data may also indicate that the user is adhering to a program of controlled activity. The data may be also indicate that the user is capable of resuming customary activity. Additionally, the changes in data such as deviations of data may preemptively indicate that the user may be experiencing a change in circumstances or conditions that may be indicative of an upcoming condition or resolution of a condition. A communication to the user 512 may also be sent to verify their activity level, such as via an electronic text message or electronic mail message.

Figure 6:
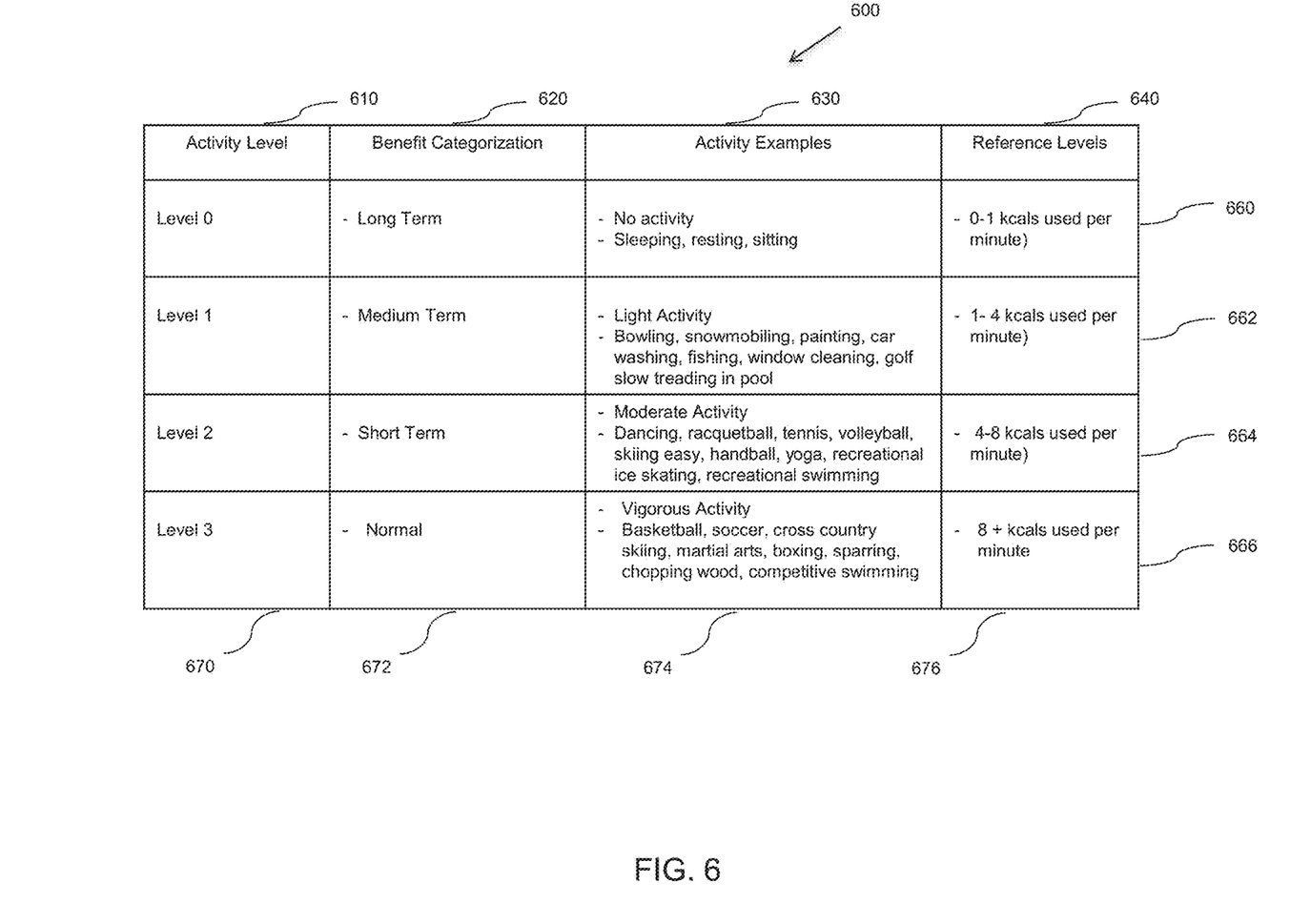
FIG. 6 shows an exemplary database structure of an embodiment of the present invention.

FIG. 6 shows an exemplary database structure 600 that may be implemented as an electronic database as described herein to support transactions related to user activity level sensor data. Database structure 600 may be implemented as an analytic, management, operational, flat-file, rational, or hierarchical database in a standalone, network, or distributed configuration or as part of a database management system (DBMS) that interact with the user, other applications, and the database itself to capture and analyze data for use in loss control and preemptive claim management such as MySQL, MariaDB, PostgreSQL, SQLite, Microsoft SQL Server, Oracle, SAP, dBASE, FoxPro, IBM DB2, LibreOffice Base and FileMaker Pro. Database 600 includes a number of database column fields 610, 620, 630, and 640 and a number of database rows 660, 662, 664, and 666. Column fields 610, 620, 630, and 640 may correspond to one or more fields such as Activity Level 610, Benefit Categorization 620, Activity Examples 630, and Reference Levels 640. In database 600, a certain activity type 670 may be associated with a certain benefit categorization 672, along with certain activity examples 674, and reference activity level data 676. For example, a short term benefit categorization may be associated with a moderate reference level of activity or caloric exertion such that if a user has a long term benefit categorization associated with them but the MEMS sensors determine that the activity level corresponds to more of a short term benefit categorization, then this may be determined to be an exception condition that may require the sensors to increase their sampling rates and frequencies. In the present invention, detected activity levels from MEMS based sensors may be correlated to database 600 in order to determine if the detected activity level matches or fall within ranges such as within column 640. If a user's activity level continually matches or falls within ranges then the user may be provided certain benefits or conversely if the user's level continually exceeds a range, the user may be monitored more on an active basis.

Figure 7:
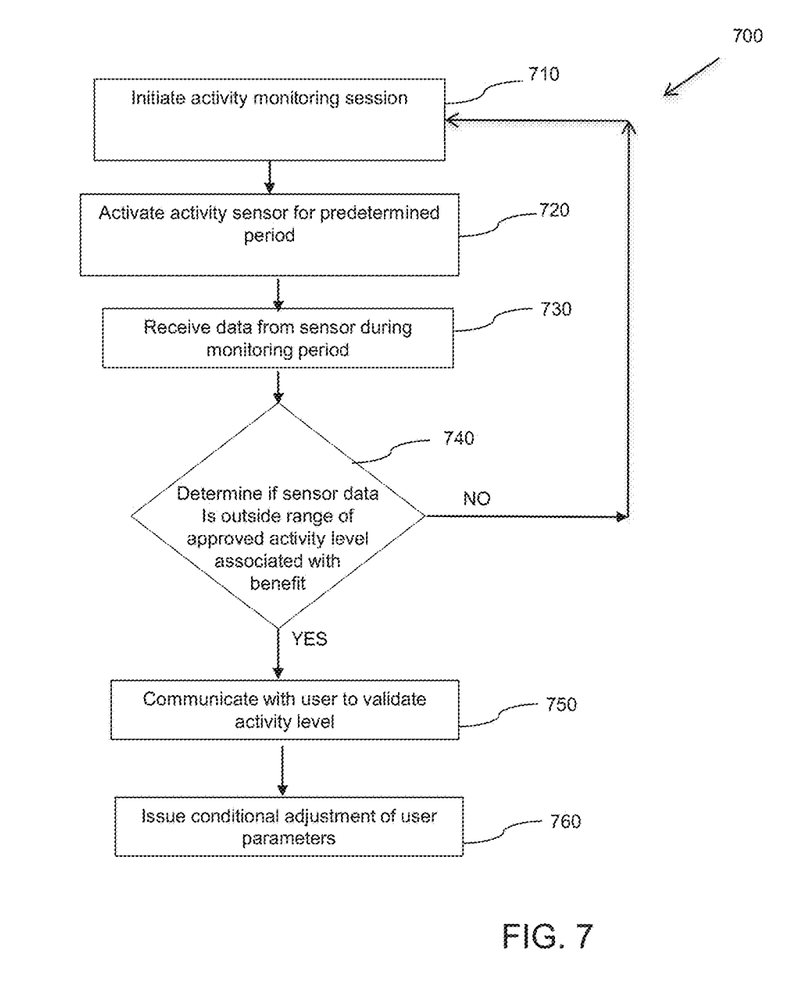
FIG. 7 shows another process flow diagram of an exemplary computer implemented method in accordance with the present invention.

FIG. 7 illustrates another exemplary computerized method 700 of the present invention. In one embodiment, the method 700 includes the step of initiating an activity monitoring session, step 710. An activity sensor is then activated for a predetermined period, step 720. Data is received from one or more sensors during a monitoring period, step 730. It is determined if the sensor data is outside an accepted or approved activity level range associated with a benefit, step 740. For example, a short term benefit may be associated with medium level of activity whereas a long term benefit may be associated with minimal levels of activity. The process continues with an electronic communication being issued to the monitored user to validate an activity level, step 750. A conditional adjustment of user parameters or data is then made, 760. User or parameters data may be a pricing parameter adjustments such as a discount or a surcharge associated with the user benefit. Parameters may also include an initial discount for simply providing the activity data such as in step 720 and/or a differential discount based on the amount of data provided or received such as during step 730 and/or the correlation of the data with historical and/or predicted activity data. In the present invention, the user may also be provided certain device or equipment, increased level of related services, recognition type information or items, or certain monetary benefits related to their condition as an incentive. Pricing may also affect a group or users as well as individual users.

Figure 8:
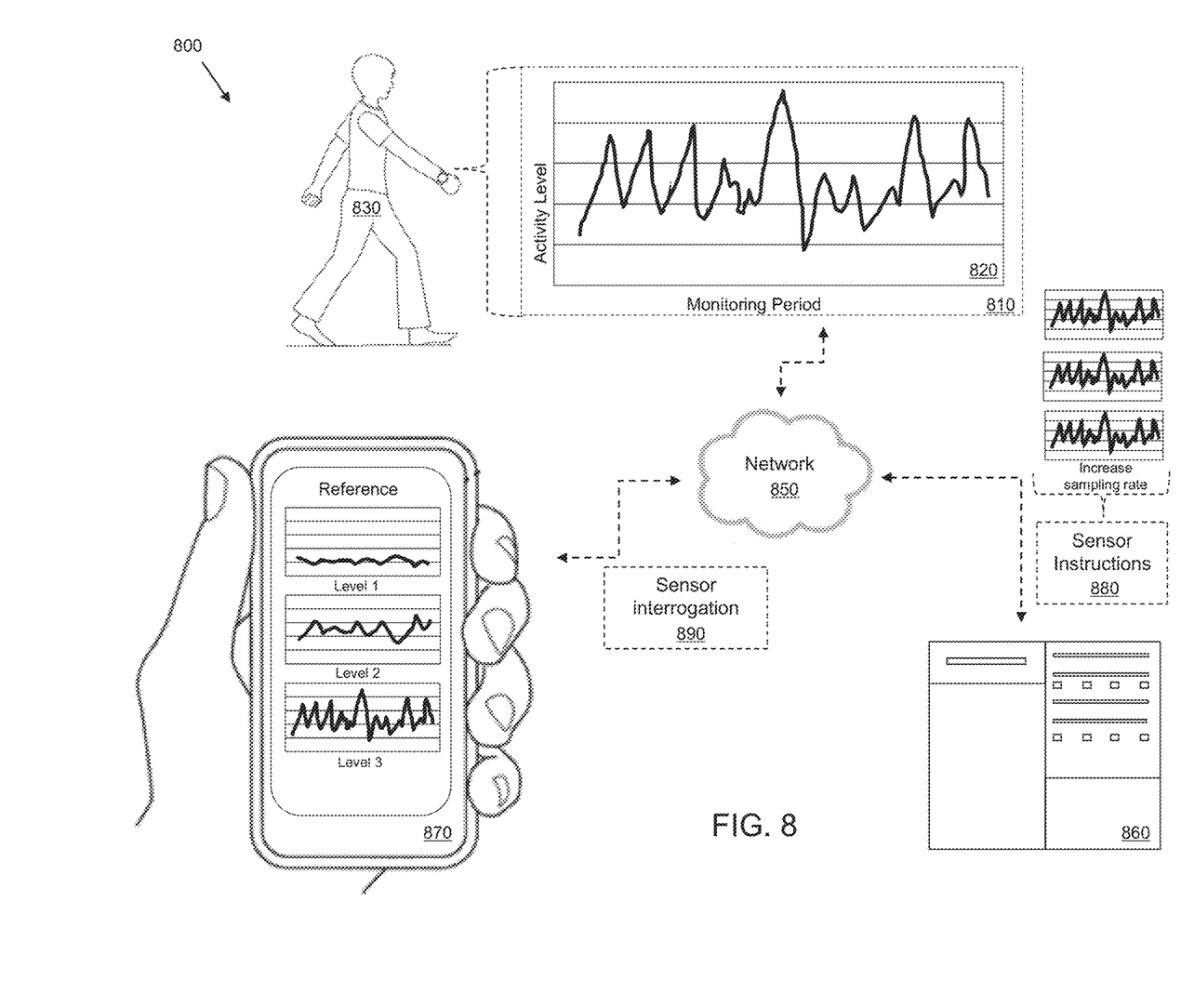
FIG. 8 shows another exemplary system of the present invention.

FIG. 8 illustrates an exemplary system implementation 800 of the present invention that includes a portable computing device 810 that is enabled to capture and transmit activity related signals 820 and data from a user 830. Portable computing device 810 includes one or more sensors that provide activity information and data 820 about the user 830 via a network 850 to a third party server or mainframe 860 and a remote computing device 870. Third party server or mainframe 860 may issue sensor instructions 880 and device 870 may also provide instructions or interrogate sensors 890 via network 850. Sensor instruction may include for example, an instruction to increase a sampling rate of the sensor device. It is contemplated that other instructions such as increasing, decreasing, starting or stopping sampling may be issued too. In operation, computing device 810 can detect various activity based events and determine an activity state of a user. In some operational modes an occurrence of an activity level can initiate a transmission of processed data to generate an audio and/or text based message to device 870. Device 870 can process received activity data to determine the occurrence of certain activity conditions or exceptions such as when a measured activity level 820 breaches a certain reference activity level such as displayed on device 870. According to various embodiments of the invention, device 870 may be configured to display charts, graphs or other visual representations of the monitored activity data. According to an embodiment of the invention device 870 is capable of retrieving supplemental information related to the user, and displaying the retrieved user information. In the present invention, a deviation or other curve fit comparison may be performed to determine a magnitude of difference between the measured activity information 820 and the reference activity information which is associated with a certain benefit for the user. Various thresholds and/or limits may be set such as via server 860 to determine if the measured activity information differs from the reference activity information.

Although the methods and features described above with reference to FIGS. 1-8 are described above as performed using the example architecture 100 of FIG. 1 and the exemplary system 200 of FIG. 2, the methods and features described above may be performed using any appropriate architecture and/or computing environment. Although features and elements are described above in particular combinations, each feature or element can be used alone or in any combination with or without the other features and elements. For example, each feature or element as described with reference to FIGS. 1-8 may be used alone without the other features and elements or in various combinations with or without other features and elements. Sub-elements of the methods and features described above with reference to FIGS. 1-8 may be performed in any arbitrary order (including concurrently), in any combination or sub-combination.

What is claimed is:

1. A non-transitory, computer-readable medium storing instructions, that, when executed by a processor, cause the processor to perform a Micro-Electro-Mechanical-System ("MEMS") based method for detecting and analyzing activity levels, the method comprising:
   collecting, by a wearable MEMS sensor, user activity data of a user wearing the MEMS sensor;
   wirelessly transmitting, from a transceiver of the wearable MEMS sensor to a mobile electronic device, the collected user activity data, wherein the mobile electronic device is adapted to display the user activity data;
   forwarding, from the mobile electronic device to a data adapter of a remote server system device via a wireless router, the collected user activity data;
   analyzing, by the remote server system device, the user activity data to determine an associated activity classification, each activity classification corresponding to a pre-determined condition and an associated condition benefit; and
   automatically generating, by a computer processor of the remote server system device, an exception condition for an investigator upon detection of a potential fraudulent condition based on a comparison of the sensed user activity data with a historical profile of that particular user's past activities and a predictive model.

2. The medium of claim 1, wherein the wearable MEMS sensor includes a nonvolatile memory having stored representations of instructions to electronically correlate the user activity data with a reference scale of activity levels.

3. The medium of claim 1, wherein the mobile electronic device includes an accelerometer and a memory having stored instructions, and a processor circuit.

4. The medium of claim 1, wherein the wearable MEMS sensor comprises at least a plurality of accelerometers capturing representations of actual user activity that are indicative of the potential fraudulent condition related to at least one of a short term disability or a long term disability.

5. The medium of claim 1, wherein the MEMS sensor generates an output signal indicative of an activity level that corresponds to a certain user condition.

6. The medium of claim 5, wherein location data is used to infer the activity level.

7. The medium of claim 6, wherein the remote server system device outputs an electronic communication to the user in the event the user condition does not correspond to the detected activity level.

8. The medium of claim 1, where the mobile electronic device electronically correlates the user activity levels with a predetermined classification of allowable activity levels, the user being provided a differential discount.

9. The medium of claim 1, wherein the mobile electronic device includes a processor circuit and a volatile memory and the processor circuit is operable to store into the volatile memory a time-window of data responsive to activity of the user, wherein the activity may qualify the user for a benefit.

10. The medium of claim 9, wherein the benefit is a pricing adjustment.

11. The medium of claim 1, wherein the MEMS sensor includes a processor and a memory, wherein and the processor is configured to generate an activity classification of the user activity.

12. The medium of claim 1, wherein the activity classification qualifies the user for a pricing adjustment.

13. The medium of claim 1, wherein the predictive model is associated with at least one of: (i) a neural network, (ii) a Bayesian network, (iii) a hidden Markov model, (iv) an expert system, (v) a decision tree, (vi) a collection of decision trees, and (vii) a support vector machine.

14. A non-transitory, computer-readable medium storing instructions, that, when executed by a processor, cause the processor to perform a Micro-Electro-Mechanical-System ("MEMS") based method for detecting and analyzing activity levels, the method comprising:
   measuring, by at least one wearable MEMS sensor configured within a mobile electronic device, user activity data, the MEM sensor including a wireless communication transceiver internal to the MEMS sensor for transmitting the user activity data;

receiving, by a remote server system device via a communications network, the user activity data;

analyzing, by the remote server system device, the user activity data to determine an associated activity classification associated with the user activity data, each activity classification corresponding to a predetermined condition and an associated condition benefit;

automatically generating, by the remote server system device, an exception condition for an investigator upon detection of a potential fraudulent condition based on a comparison of the sensed user activity data with a historical profile of that particular user's past activities and a predictive model; and determining, based on the determined activity classification, a content of one or more electronic communications transmitted by the remote server system device to a user device.

15. The medium of claim 14, wherein the electronic communication is configured for display on the mobile electronic device.

16. The medium of claim 15, wherein the determined activity classification is based on historical analysis of activity levels associated with a variety of conditions.

17. The medium of claim 16, wherein the conditions relate to a sedentary or an active condition that are correlated with a compliant and a non-compliant classification.

18. The medium of claim 14, wherein the wearable MEMS sensor includes a nonvolatile memory having stored representations of instructions to electronically correlate the user activity data with a reference scale of activity levels.

19. The medium of claim 14, wherein the mobile electronic device includes an accelerometer and a memory having stored instructions, and a processor circuit.

20. The medium of claim 14, wherein the wearable MEMS sensor comprises at least a plurality of accelerometers capturing representations of actual user activity that are indicative of the potential fraudulent condition related to at least one of a short term disability or a long term disability.

21. The medium of claim 14, wherein the MEMS sensor generates an output signal indicative of an activity level that corresponds to a certain user condition.

22. The medium of claim 21, wherein location data is used to infer the activity level.

* * * * *